(12) United States Patent
Järnefelt et al.

(10) Patent No.: US 10,576,296 B2
(45) Date of Patent: Mar. 3, 2020

(54) NAVIGATED TRANSCRANIAL MAGNETIC STIMULATION PLANNING USING A STRUCTURAL EFFECTIVENESS INDEX

(71) Applicant: Nexstim Oy, Helsinki (FI)

(72) Inventors: Gustaf Järnefelt, Helsinki (FI); Petro Julkunen, Helsinki (FI)

(73) Assignee: Nexstim Oyj, Helsinki (FI)

( * ) Notice: Subject to any disclaimer, the term of this patent is extended or adjusted under 35 U.S.C. 154(b) by 526 days.

(21) Appl. No.: 14/774,704

(22) PCT Filed: Mar. 23, 2015

(86) PCT No.: PCT/FI2015/050194
§ 371 (c)(1),
(2) Date: Sep. 11, 2015

(87) PCT Pub. No.: WO2015/140413
PCT Pub. Date: Sep. 24, 2015

(65) Prior Publication Data
US 2016/0106995 A1   Apr. 21, 2016

Related U.S. Application Data

(60) Provisional application No. 61/968,446, filed on Mar. 21, 2014.

(51) Int. Cl.
*A61N 2/00* (2006.01)
*A61N 1/02* (2006.01)
*A61N 2/02* (2006.01)

(52) U.S. Cl.
CPC ............... *A61N 2/006* (2013.01); *A61N 1/02* (2013.01); *A61N 2/02* (2013.01)

(58) Field of Classification Search
CPC .................................. A61N 2/006; A61N 2/02
See application file for complete search history.

(56) References Cited

U.S. PATENT DOCUMENTS

| | | | |
|---|---|---|---|
| 2003/0050527 A1 | 3/2003 | Fox et al. | |
| 2005/0228209 A1 | 10/2005 | Schneider et al. | |
| 2008/0262338 A1 | 10/2008 | Paitel et al. | |

FOREIGN PATENT DOCUMENTS

| | | |
|---|---|---|
| CN | 101516444 A | 8/2009 |
| CN | 103429146 A | 12/2013 |
| JP | 2005169087 A | 6/2005 |
| JP | 2009536073 A | 10/2009 |

(Continued)

*Primary Examiner* — Christine H Matthews
(74) *Attorney, Agent, or Firm* — Seppo Laine Oy (57) ABSTRACT

Described herein are methods including determining a structural effectiveness index (SEI) for a target area of a brain which accounts for the effectiveness of a Transcranial Magnetic Stimulation (TMS) pulse based on at least one neurological feature of the brain. An SEI may include an anisotropy index (AI). An AI may account for the effectiveness of a TMS pulse based at least on the local anisotropy of the target area. An SEI may include a connectivity index (CI). A CI may account for the effectiveness of a TMS pulse at a different location of the brain than a stimulated target area. Moreover, the CI can be based at least partially on white matter tract connections. The SEI of at least one area of a brain may be used in order to plan a minimum effective dose at that location based on the actual neurological structure there, e.g. the anisotropy or white matter tracts at that area.

25 Claims, 2 Drawing Sheets

(56) References Cited

FOREIGN PATENT DOCUMENTS

| WO | WO2008031847 A1 | 3/2009 |
| WO | WO2012164172 A1 | 12/2012 |
| WO | WO2012164173 A2 | 12/2012 |

NAVIGATED TRANSCRANIAL MAGNETIC STIMULATION PLANNING USING A STRUCTURAL EFFECTIVENESS INDEX

FIELD OF INVENTION

The present invention relates to the field of Transcranial Magnetic Stimulation (TMS). Certain embodiments of the present invention relate to navigated TMS (nTMS) and planning thereof.

BACKGROUND OF INVENTION

During TMS planning and stimulation it is desired to induce the minimum effective dose of stimulation at any given place in the brain. By giving a dose which is lower than the minimum effective dose it is likely that the dose will not have the intended effect. By giving a dose which is much larger than the minimum effective dose has multiple side effects. Examples of some are the over stimulation of an area, the stimulation of a larger area than intended, the accumulation of excess dose in an area or region which limits the length of a stimulation session, the overheating of an area of the brain and the possibility of seizures.

It is possible to experimentally determine the minimum effective dose for certain areas of the brain, e.g. within the motor cortex, where the effect of the stimulation can be measured or observed. It is typical to then use that minimum effective dose as a guideline for other areas of the brain, either replicating that dose or increasing that dose by a predetermined amount, e.g. stimulating another region with 120% of the minimum effective dose for the other region. Typically, general rules of thumb are applied and there is no correlation between the dose which is administered and the actual minimum effective dose for each non-measurable location.

One of the key features of how effective a dose will be is the neural structure of the area to be stimulated and the relative orientation of an induced electric field to that area. Currently, TMS and nTMS systems do not take into account this information, resulting in inefficient and ineffective doses of stimulation being applied. It is therefore a desire to have a system and method which accounts for the neural structure at a stimulation location in order to determine a minimum effective dose and/or orientation. Additionally, it is desirable to understand the actually effectiveness of a dose at a location in or on the brain which is not easily measurable.

SUMMARY OF THE INVENTION

It is an aspect of certain embodiments of the present invention to provide methods of navigated Transcranial Magnetic Stimulation (nTMS) planning and/or nTMS stimulation.

Examples of such methods include the steps of: determining a structural effectiveness index (SEI) for a target area of a brain which accounts for the effectiveness of a Transcranial Magnetic Stimulation (TMS) pulse based on at least one neurological feature of the brain, determining a base electric field amplitude and orientation for the brain, and calculating an intended induced electric field vector for the target area of the brain based on the SEI for said target area and the base electric field amplitude and orientation for the brain.

According to certain examples, the SEI includes an anisotropy index (AI). An AI may account for the effectiveness of a TMS pulse based at least on the local anisotropy of the target area. Additionally, according to certain examples, the SEI includes a connectivity index (CI). A CI may account for the effectiveness of a TMS pulse at a different location of the brain than a stimulated target area. Moreover, the CI can be based at least partially on white matter tract connections.

An SEI can have an AI component and a CI component. Additionally, an SEI may only be an AI component or a CI component. Furthermore, an SEI may contain or consist of other indexes relating to the structural effectiveness of TMS, for example a fractional anisotropy indec (FIA). The SEI may be a vector, a numerical value, a function of an angle (such as a coil angle or an induced electric field angle with respect to a SEI vector), or a direction.

According to certain examples, methods include the step of calculating at least one position and orientation of a TMS coil device in relation to a brain capable of inducing an intended induced electric field for a target area of the brain. Additional steps may include determining pulse parameters for at least one coil winding of a TMS coil device such that the pulse parameters are capable of causing the TMS coil device to induce an intended induced electric field for a target area of a brain.

According to certain embodiments and examples, it is desired to use the SEI of at least one area of a brain in order to plan an effective and/or minimum effective dose at that location based on the actual neurological structure there, e.g. the anisotropy or white matter tracts at that area.

According to certain embodiments and examples, it is desired to use the SEI of at least one area of a brain in order to plan an effective and/or minimum effective dose at another location which has a similar neurological structure as the other.

According to certain embodiments and examples, it is desired to use the SEI of at least one area of a brain in order to determine the effectiveness of a certain dose or doses at that location based on the actual neurological structure there and the orientation of the doses.

According to certain embodiments and examples, it is desired to use the SEI of several areas of a brain in order to select an optimal area to stimulate for a desired effect, based on the actual neurological structure at one or more of the areas.

Furthermore, it is an aspect of certain embodiments of the present invention to provide a non-transitory computer readable medium having stored thereon a set of computer implementable instructions for causing a processor to carry out the methods described herein.

Still yet, it is an aspect of certain embodiments of the present invention to provide a navigated Transcranial Magnetic Stimulation (nTMS) system comprising a processor configured to determine a plan for or to execute nTMS in accordance with the methods described herein.

DETAILED DESCRIPTION OF EXEMPLARY EMBODIMENTS

According to certain embodiments there are herein disclosed methods of navigated Transcranial Magnetic Stimulation (nTMS) planning. The methods herein can be used to create a plan for later administration of TMS to a patient. The methods herein can also be used during administration of TMS to a patient when planning the next and/or a future stimulation.

According to certain methods, planning for nTMS includes the steps of determining structural effectiveness index (SEI) for an area or volume of a brain. The SEI can account for the effectiveness of a TMS pulse based on at least one neurological feature of the brain. Examples of such neurological features are: the neuronal isotropy or anisotropy of an area of the brain, the orientation of neuronal bundles, a number or average number of neuronal bundles, connectedness of one area to another; number, density and/or thickness of white matter tracts at an area or a combination thereof. Additional examples will become apparent throughout the present description.

According to certain examples, the SEI may contain an anisotropy index (AI), a connectivity index (CI), a combination of the two and/or a generalized index which takes into consideration the factors of either or both of the AI and CI. The SEI, AI and/or CI can be vectors or represented thereby. They may also be merely numerical indexes. Generally, the AI accounts for the effectiveness of a TMS pulse based at least on a local anisotropy of an area. Similarly, generally the CI accounts for the effectiveness of a TMS pulse, when applied to a first area, at a different second area. The first area is typically on or near the cortex. The second area can also be on or near the cortex, but it can also be a deeper area of the brain.

Methods can further include the steps of determining a base electric field amplitude and orientation for the brain, and calculating a desired or intended induced electric field vector for the area of the brain based on the SEI for said area and the base electric field amplitude and orientation for the brain.

According to certain examples, the order of steps may be changed. For example, according to certain methods the SEI can determined and/or mapped for a certain area and/or region of the brain. Following that a base electric field amplitude and orientation can be determined. For example, a base electric field amplitude can be a motor threshold (MT) and the base orientation can be perpendicular to a brain topological feature. Similarly, the base electric field amplitude and orientation can be determined followed by determining the SEI for a certain area and/or region of the brain.

As discussed herein, an area or target area refers to the focal spot of an intended TMS pulse. The term area here is synonymous with volume as the focal spot is typically three-dimensional. A region or treatment region refers to a larger area than a target area which contains several possible target areas. Similarly, a region or treatment region is synonymous with a treatment volume. Therefore, a region or treatment region is larger than a target area.

The determining steps disclosed herein can be carried out by, for example, experimentation (when possible), calculation, recalculation, adjusting, optimization, importation of the relevant data from a separate device/system, or a combination thereof.

Some methods of planning and administering TMS pulses to a subject assume that a target area of the subject's brain is isotropic, i.e. that the brain matter in that area is randomly oriented. Other methods of planning and administering TMS pulses to a subject assume that a target area of the subject's brain is perfectly anisotropic, i.e. that the brain matter in that area is perfectly aligned in the same direction. However, the orientation of brain matter in any given area of the brain typically is not uniform but does have a bias in some direction or directions. As such, any given area of the brain is anisotropic, i.e. the brain matter is not completely randomly oriented.

When inducing an electric field in an area of a brain, e.g. by TMS, the effect of that electric field is highly dependent on the orientation of the electric field in relation to the orientation of the brain matter which is being effected. TMS stimulation activates neuronal bundles which are parallel to the electric field and bundles with bends. Additionally, responses which have been evoked from TMS can be affected by physiological factors. The effects of these physiological factors may be so great as to overpower the influence of the underlying neuronal structure.

Figure 1:
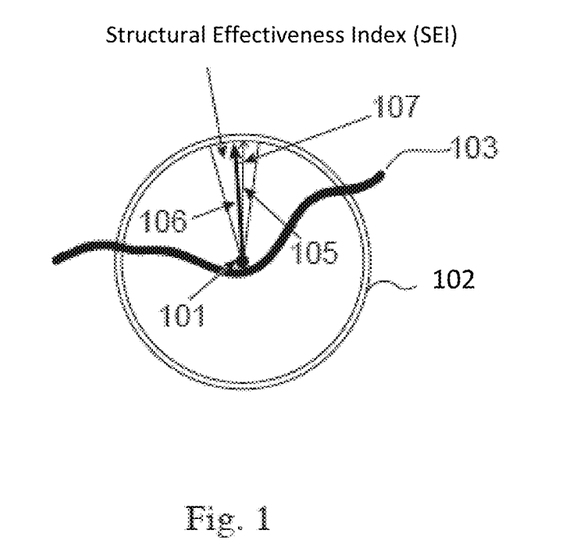
FIG. 1 shows a graphical representation of a SEI in association with an example nTMS stimulation.

As can be seen in FIG. 1, it is common that a target area 101 of a brain is on or near a sulcus 103, e.g. the central sulcus. When assuming that the neuronal bundles of the target area 101 are perfectly uniform, e.g. around the sulcus, then the ideal orientation of an electric field vector 105 is perpendicular to the sulcus 103 and thus parallel to the anisotropy of the target area 101.

Figure 2:
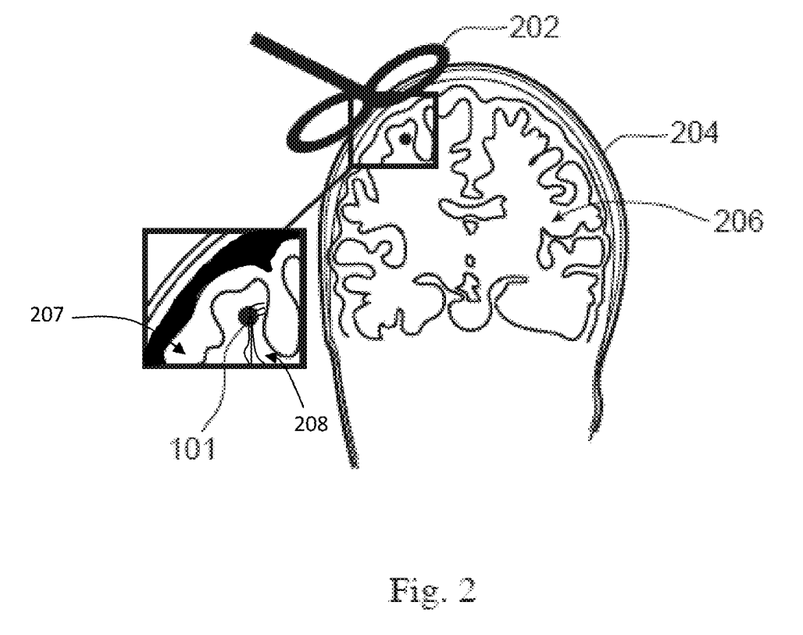
FIG. 2 shows an example of neuronal structures of a brain, including a more detailed insert of an area near a target area for stimulation.

As can be seen in FIG. 2, the structure of a brain 204 can be quite complex near a target area 101 to receive a dose from a coil device 202 of a nTMS system. Grey matter 207, white matter 206 and their boundaries, as shown with lines, effect TMS effectiveness. The anisotropy, for example of the grey matter 207, can be accounted for in an SEI with, for example, an AI component of the grey matter 207 at or near the target area 101. Similarly an AI component can form a part of the SEI for the white matter 207 at or near the target area 101. Still yet, white matter tracts 208 at or near the target area 101 can be accounted for in a CI component of the SEI. The CI component may be a vector and/or a indication of a position where the bends in the tracts 208 are located.

As described herein, the anisotropy of an area of a brain is the actual orientation/bias of the brain matter within the area. The anisotropy can be determined in several ways, e.g through diffuser tensor imaging (DTI), diffusion kurtosis imaging (DKI), observation of white matter tracts in imaging or modeling, observation of grey matter orientation in imaging or modeling, observation of the surface curvature of the cortex in imaging or modeling, etc. Furthermore, the anisotropy can be determined using image recognition software of MRI, DTI, DKI, Ultrasound or other images in order to categorize the anisotropy of an area or region.

As described herein, the anisotropy index (AI) can be an index value, e.g. a numerical value, which is determined from and/or representative of the anisotropy of an area of a brain. Thereby, the AI can be utilized in calculations for nTMS planning. According to certain examples, the AI is a representation of the difference of an area from a random distribution or isotropy. As an example, an AI of 0 can be an area which is isotropic and an AI of 1 would be an area which is 100% biased in a specific direction. However, in practice, AI's of 0.7 to 0.9 are common between such a 0-1 scale. It will be appreciated however that other scales can be used without departing from the scope of the present invention.

The SEI and/or AI can also be a vector. The AI vector can represent the optimal orientation for stimulation at an area based on the anisotropy of the area. As shown in FIG. 1, the AI 106 is a vector. The AI vector 106, with the optimal stimulation direction is at an angle 107 (α) from the perpendicular vector 105, which assumes perfect anisotropy. The magnitude of the vector can represent the effectiveness of a stimulation in the AI vector direction based on the anisotropy of the area. As an example, if neuronal bundles at a target area are generally, but not uniformly, in a certain direction, and due to this specific non-uniformity a stimulation in the certain direction would only be 90% effective, the AI vector could be in the certain direction with a magnitude of 0.9.

Additionally, the SEI and/or AI can be a function of the angle between an intended stimulation direction and an anisotropy angle. Following the example above, if the AI vector is in a certain direction the magnitude is 0.9, but if an intended stimulation is to be made 5 degrees offset from the direction, the effectiveness of the stimulation drops to 75%, then the AI for the certain direction plus/minus 5 degrees would be 0.75. Examples of this can be seen, for example in the graph of FIG. 4. As such, in the example of FIG. 1, the SEI is shown as a range around the optimal vector 106 which is dependent on the angle α between the induced electric field and the optimal direction 106.

According to certain embodiments, a treatment region 102 can be identified. Within the treatment region 102 can be a plurality of potential target areas 101. The anisotropy of target areas 101 within the treatment region 102 may vary. As the result of TMS is impacted based on the anisotropy of the target area 101, e.g. based on the neuronal microstructure and orientation thereof, it is beneficial to know how the anisotropy of a particular target area 101 relates to other target areas. Based on this information, one or more optimal target area(s) 101 can be determined within a treatment region 102 and/or stimulation parameters for a specific target area 101 can be optimized.

In order to optimize treatment efficiency or specificity of TMS, it is valuable to induce the smallest effective electric field in a given treatment region 102. The higher a dose is the larger the area of the brain is which is affected. Therefore, keeping the dose to the smallest effective amount reduces the stimulation of unintended areas of the brain. Additionally, the lower each dose is the more doses which can be administered while staying within a safe amount of stimulation to the surrounding region of the brain.

Typically, a MT is determined at the beginning of a nTMS session. While a person may have a known MT which is used/reused over multiple TMS sessions, the MT can be determined each time. Often, the MT is a resting MT. The MT is typically a minimum stimulation intensity normalized to the maximum output power of the stimulator or minimum effective amplitude of an electric field which is sufficient to elicit a motor response from the subject. Other less common thresholds apply a similar principle but the measured/observed response varies.

The MT is typically determined with an induced electric field which is perpendicular to the central sulcus. However, in accordance with examples of the present invention the SEI, which can include the AI, can be determined once for the MT site. While the amplitude of the MT may vary over time for a patient, the anisotropy of that area of the brain should not vary greatly. Therefore, if the optimal orientation and/or effectiveness of stimulation of determining the MT is found once for a patient, that same orientation can be reused in future MT determination steps. Such an implementation can increase the speed and reliability of determining the MT of a patient.

For areas of the brain, like the Motor Cortex, where responses to stimulation can be measured and/or observed, it is possible to calculate experimentally for any given target location an actual most effective stimulation amplitude and orientation. However, even though it is possible, it is not necessarily practical to do so. Therefore, once a MT is calculated for an individual, that value is typically used as a base electric field amplitude for the brain. Additionally, as described above, the base electric field amplitude for the brain may be a standard MT calculation or it may be an MT which takes into account the SEI, AI and/or CI for that target area. When targeting other regions of the brain the stimulation amplitude can be considered as a function of the MT, or base electric field amplitude. As an example, if the MT is known for a patient, when stimulating a target area 101 an amplitude of 105% or 120% of the MT can be used. The increase in amplitude over the base amplitude can be to insure that the resulting stimulation is effective.

Several factors affect how effective a given stimulation will be. The neuronal microstructure, which can be characterized by the anisotropy of the target area will have an effect on the effectiveness of a given pulse. Therefore, without necessarily taking these factors into account, a user has as a rule of thumb just added an amount, e.g. 20%, to the MT amplitude when targeting another area or region of the brain. The result of this is that in some cases, an increase of 20% is not sufficient to have a desired effect. In other cases, an increase of 20% is significantly more than necessary and the operator is subjecting the patient's brain to an unnecessary amount of stimulation. Adjusting and selecting the stimulation intensity desirable, since intensity which is higher than necessary activates a large area of the brain than desired, while intensity which is too low may not be effective enough to guarantee cortical neuronal activation.

Figure 3:
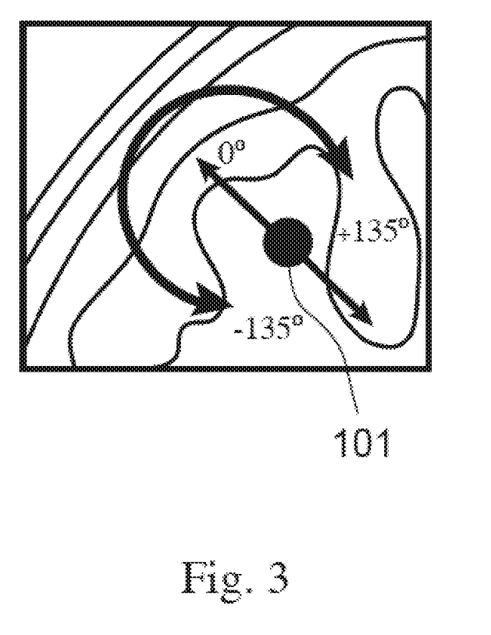
FIG. 3 shows an example of a method for experimentally calculating an AI for an target area.

Therefore, according to certain examples, an SEI, which may contain an anisotropy and/or an AI can be utilized to provide better calculations for a necessary induced electric field at a given target area. For example, when the MT is calculated, an AI for that target area can also be calculated. As mentioned above, the MT is typically calculated with induced electric fields perpendicular to the central sulcus. As shown in FIG. 3, for example, once a MT is determined, using the determined MT and rotating the induced electric field through a plurality of angles an AI can be calculated for that target area. The AI can be calculated from motor evoked potentials (MEPs) as a function of the induced electric field angle from the topological feature, e.g. the sulcus.

Additionally, the by applying pulses at a plurality of angles at the same spot, an actual optimal electric field orientation can be determined. As seen for example in FIG. 1, a base electric field vector 105 having a base orientation which is perpendicular to the central sulcus 103 is not the optimal orientation. Based on the anisotropy of the target area, the optimal orientation 106 is offset from the base orientation by an angle α.

At a given target area, the effective amplitude of an induced electric field can equal the product of the AI, the base electric field amplitude (e.g. MT) and the cosine of α (e.g. the difference between the base electric field angle and the optimal orientation 106).

For the target area where the MT was determined, the anisotropy can be determined. This can be before or after calculating of the MT and/or AI. The anisotropy for that target area can then be compared to the anisotropy of other target areas, for example in a treatment area. In examples where the treatment area is a portion of the brain which does not have any easily directly measureable or observable traits, a desired induced electric field vector can be calculated based on the AI for the target area and the base electric field amplitude and orientation.

For portions of the brain where a response to a stimulus can be measured, e.g. within the motor cortex, the AI for any given location can be directly measured and/or calculated. An example of this is shown with FIGS. 3 & 4. For example, at a given target area 101 of FIG. 3, multiple stimulation pulses can be administered to the same target area 101 but with various orientations ranging from, for example, plus/ minus 135 degrees from an initial orientation, 0. The initial orientation can be perpendicular to a known brain topological feature(s) such as the central sulcus.

Figure 4:
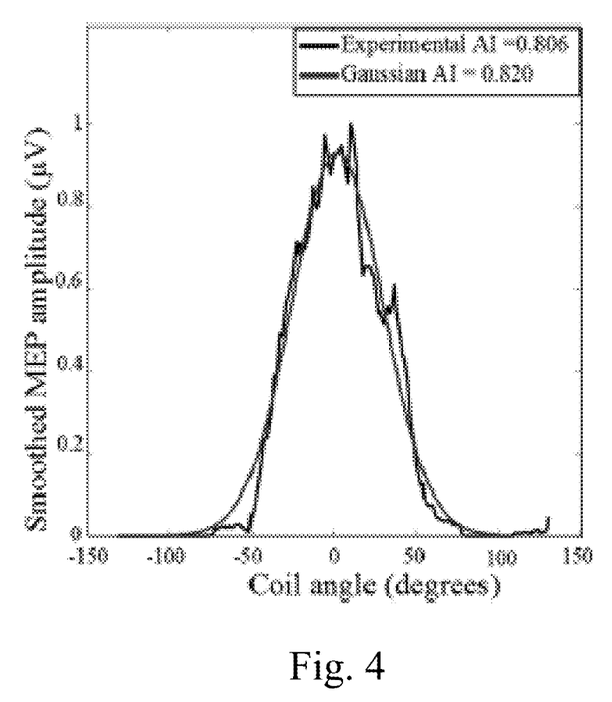
FIG. 4 shows graphical results of the AI determined in the method as shown in FIG. 3.

Results from an example AI determination as shown in FIG. 3 can be seen in FIG. 4. At each angle a single TMS pulse was administered and the resulting motor evoked potential (MEP) was measured and plotted. The results show that as the angle varies from an optimal angle, the effectiveness of the pulse rapidly diminishes. By applying a Gaussian function to the results an AI for the target area 101 can be determined. As can be further seen in FIG. 4, the amplitude of the AI can be dependent on the angle from the optimal.

Where the SEI of a target area cannot be easily experimentally determined, the SEI can be calculated in other ways. For example, the SEI for an area of a brain can include calculating an SEI from DTI of the brain, DKI and/or considering the connectivity of white matter tracts within the area of the brain, for example from tractography. Additionally, calculating the SEI for an area of the brain can be based on directions of bends of neuronal bundles within said area and/or on a known or average number of neuronal bundles within the area.

Another example of determining the SEI for a particular target area of the brain is to determine an SEI for a first area of a brain (e.g. the target area used for an MT determination) and then using that determined SEI for a second area of the brain (e.g. within the treatment region). Additionally, based on a known and/or assumed characteristic of a second area, which is different from the corresponding characteristic of the first area, the AI for the first area of the brain can be modified to fit the second area of the brain.

Additionally, determining the SEI for an area of the brain can include calculating or estimating an anisotropy of said area of the brain, identifying a different portion of the brain with a similar anisotropy, calculating an SEI for said different portion of the brain, and using said calculated SEI for said different portion of the brain as the SEI for said area of the brain. For example, if the SEI, AI and/or the anisotropy for the target area where the MT was calculated is known, and wherein a treatment region has multiple suitable target areas therein with different SEI's, then a specific target area can be chosen to be stimulated based on finding a suitable target area with the most similar SEI compared to the MT target area. In this manner, the expected effectiveness of the stimulation from the measured MT target area can be expected to be replicated in the new area.

Similarly, if a specific target area is desired to be used in an area of the brain with no easily measurable or observable response, a location in another area of the brain, e.g. the motor cortex, can be found with a similar neurological features, anisotropy, AI, CI or combination thereof. In that similar area, the AI and/or angle α can be determined and then that information used with respect to the specific target area which is desired to be used.

Furthermore, in a planning stage, for an treatment region, the SEI can be mapped for a portion or for the whole treatment region. Specific target areas can be identified based on the mapping where the least induced electric field will be required to have a desired effect. In this manner, the total amount of exposure of the brain to induced electric fields can be minimized with a maximum effect, e.g. maximum neuronal stimulation effect.

As discussed above, determining a base electric field amplitude and orientation, or base electric field vector, can be using a pre-selected and/or default orientation, e.g. perpendicular to a brain topological feature, along with a determined MT. Additionally, determining a base electric field amplitude and orientation for the brain can include determining a theoretical optimum induced electric field for an area of the brain which does not account for the anisotropy of said area.

Calculating a desired or intended induced electric field vector for the area of the brain can include modifying the amplitude of the base electric field based on the determined SEI. Calculating the desired induced electric field vector for the area of the brain may also, or on its own, include selecting an angle which is other than perpendicular to a brain topological feature, such as a sulcus, based on the SEI, anisotropy and/or AI.

Furthermore, methods may include additional steps. For example, according to certain examples, the method includes the steps of: identifying a region of the brain including said area of the brain, wherein both the region and area of the brain share at least one function, determining at least one additional SEI for at least one additional area of the brain within said identified region, determining an optimal area of the brain, within said identified region of the brain based on the determined SEI for each region, and wherein calculating a desired induced electric field vector is for the optimal area of the brain.

According to certain examples, a method includes the step of calculating at least one position and orientation of a TMS coil device in relation to the brain capable of inducing said desired induced electric field for the area of the brain. Still yet, a method can include the step of determining pulse parameters for at least one coil winding of a TMS coil device such that the pulse parameters are capable of causing the TMS coil device to induce the desired induced electric field for the area of the brain. Pulse parameters can include pulse amplitude, duration and direction, among others.

Furthermore, fractional anisotropy (FA) can be used in the determination of the SEI and/or the AI. Additionally, there can be a fractional anisotropy index (FAI) which is used on its own, in place of other indexes described herein, or as a portion of the SEI. The FA or FAI can be determined from, e.g. a spherical (or other shaped) volume under a stimulation, or intended stimulation, target area considering the plane of FA values perpendicular to TMS coil. FA can be used to measure and/or calculate the anisotropy of diffusion channels within white matter. For instance, the higher the FAI, e.g. closer to 1 in a 0-1 scale, the higher the directionality of the diffusion. If the FAI is 0 or close to 0 then the diffusion has little or no preferred direction. According to certain examples, AI is a measure or neuronal directionality and organization, e.g. via electromagnetic inductions. According to certain examples, the FAI is a measure of fluid (e.g. water) diffusion. FA can typically be computed based on images gathered with at least 12 diffusion directions. Therefore, FA maps can be generated and FAI presented as either values and/or vectors. FA and FAI can also be determined with tractography.

According to certain embodiments there is a transitory and/or non-transitory computer readable medium which has stored thereon a set of computer implementable instructions for carrying out any of the methods disclosed herein.

Furthermore, according to certain embodiments there is disclosed a system which includes a processor configured to carry out any of the methods disclosed herein. The system may further include nTMS components, such as a TMS coil device.

In accordance with the methods and embodiments discussed above, it is possible to change the dose of electric field stimulation to a patient based on the tractography of an area. As such, the SEI can include a CI component or the SEI can be only a CI. Thus, the SEI and/or CI be a function of and/or representative of the connectivity of an area. For example, a target area in a treatment region with twice as many white matter tracts connecting to another region of the brain may have a CI or CI component which is two times greater than a target area with only half the white matter tracts. The CI or CI component can be linear between the different target areas based on connectivity or it may be based on another function and/or additional parameters. Therefore, in such an example, if both areas are to be stimulated, the necessary induced electric field amplitude for the area with twice the white matter tracts need not be as large as the area with only half.

Similar to the discussion of the number of white matter tracts, the same can be applied to the thickness of tracts, thickness of a bundle of tracts, average number of tracts in the area or a combination thereof. Still yet, any other representation about the relative quality of connectedness, e.g. based on white matter tracts, which can be determined through tractography, for instance, can be used with the methods disclosed herein. The connection and/or CI can be characterized by the number, or size of a cross section, of grey and/or white matter tracts that connect two areas. The CI can be determined relative to a known connection, such as the motor area of a hand, leg or other body part. The CI can also be determined relative to the connectivity of tracts to deeper structures of the brain. The amount of tracts and/or the cross section area of the tracts can be used to determine a relative amount of stimulation required for successful stimulation when using the base stimulation, e.g. MT, with a known connectivity and/or CI at another location with either a similar or different known connectivity and/or CI. Furthermore, the CI can be a vector with a direction which is, for example, representative of the direction or average direction of bends in tracts, white matter or grey matter tracts.

As can be seen by such a case, according to certain examples, the higher an SEI, AI, CI, FAI or combination thereof for a given area, the lower the necessary stimulation energy or dose. However, of course, by simply using another formula or definition of the indexes described herein, a lower index value can also represent a lower necessary dose. What is to be understood however is that the better the connectivity of an area compared to another the lower the necessary dose. Similarly, the more anisotropic an area is, the less dose is required as long as the induced electric field is aligned in the optimal orientation. Herein, dose can be interpreted as being equivalent to an amplitude of an induced electric filed.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A method of navigated Transcranial Magnetic Stimulation (nTMS) planning comprising the steps of:
    determining a structural effectiveness index (SEI) for a target area of a brain which accounts for effectiveness of a Transcranial Magnetic Stimulation (TMS) pulse based on at least one neurological feature of the brain, the SEI being a function including a calculated anisotropy index (AI) representative of an anisotropy of a neuronal structure within the target area,
    delivering an initial TMS pulse to the brain,
    determining a base electric field amplitude and orientation for the brain based at least partially on the delivered initial TMS pulse, and
    calculating an intended induced electric field for the target area of the brain based on the SEI for said target area and the base electric field amplitude and orientation.

2. The method of claim 1, further comprising the step of:
determining pulse parameters for at least one coil winding of a TMS coil device such that the pulse parameters are capable of causing the TMS coil device to induce the intended induced electric field for the target area of the brain.

3. The method of claim 2, wherein a pulse amplitude parameter is determined based on a magnitude of the SEI for the target area.

4. The method of claim 1, wherein the SEI is a vector.

5. The method of claim 1, wherein determining a base electric field amplitude and orientation for the brain includes determining a Motor Threshold (MT) for the brain with an orientation perpendicular to a sulcus.

6. The method of claim 1, wherein determining a base electric field amplitude and orientation for the brain includes determining a theoretical optimum induced electric field for said target area of the brain without accounting for anisotropy of said area.

7. The method of claim 1, wherein calculating the intended induced electric field for the target area of the brain includes modifying the amplitude of the base electric field amplitude based on the determined SEI.

8. The method of claim 1, wherein calculating the intended induced electric field for the target area of the brain includes selecting an angle other than perpendicular to a brain topological feature.

9. The method of claim 1, wherein the anisotropy index (AI) is directional.

10. The method of claim 9, wherein the anisotropy index (AI) is represented with a principal vector.

11. The method of claim 1, wherein the SEI function includes a consideration of the angle between the intended induced electric field and a direction in which the anisotropy index is highest.

12. A non-transitory computer readable medium having stored thereon a set of computer implementable instructions for causing a processor to carry out a method of navigated Transcranial Magnetic Stimulation (nTMS) planning comprising the steps of:
determining a structural effectiveness index (SEI) for a target area of a brain which accounts for effectiveness of a Transcranial Magnetic Stimulation (TMS) pulse based on at least one neurological feature of the brain, the SEI being a function including a calculated anisotropy index (AI) representative of an anisotropy of a neuronal structure within the target area,
determining a base electric field amplitude and orientation for the brain, and
calculating an intended induced electric field for the target area of the brain based on the SEI for said target area and the base electric field amplitude and orientation.

13. The non-transitory computer readable medium of claim 12, wherein the SEI includes a connectivity index (CI) which accounts for the effectiveness of a TMS pulse at a different location of the brain than a stimulated target area, and wherein the CI is based at least partially on white matter tract connections.

14. The non-transitory computer readable medium of claim 12, wherein the method further comprises the steps of:
identifying a treatment region of the brain including said target area of the brain, wherein both the treatment region and target area of the brain share at least one function,
determining at least one additional SEI for at least one additional target area of the brain within said identified treatment region,
determining an optimal target area of the brain, within said identified treatment region of the brain based on the determined SEI for each target area, and
calculating an intended induced electric field vector for the optimal target area of the brain.

15. The non-transitory computer readable medium of claim 12, wherein the method further comprises the step of:
calculating at least one position and orientation of a TMS coil device in relation to the brain capable of inducing said intended induced electric field vector for the target area of the brain.

16. The non-transitory computer readable medium of claim 12, wherein the method further comprises the step of:
determining pulse parameters for at least one coil winding of a TMS coil device such that the pulse parameters are capable of causing the TMS coil device to induce the intended induced electric field vector for the target area of the brain.

17. The non-transitory computer readable medium of claim 16, wherein a pulse amplitude parameter is determined based on a magnitude of the SEI for the target area.

18. The non-transitory computer readable medium of claim 12, wherein calculating the AI includes calculating an AI from at least one of Diffusion Tensor Images (DTI) and Diffusional Kurtosis Imaging (DKI) of the brain.

19. The non-transitory computer readable medium of claim 12, wherein calculating the AI is based on directions of bends of neuronal bundles within the target area.

20. The non-transitory computer readable medium of claim 12, wherein calculating the AI is based on a known or average number of neuronal bundles within the target area.

21. The non-transitory computer readable medium of claim 12, wherein the SEI includes a Connectivity Index (CI), and wherein the method further comprises the step of determining the CI for a target area of the brain, which is based on tractography.

22. The non-transitory computer readable medium of claim 12, wherein determining the SEI for a target area of the brain includes determining an SEI for a first area of the brain and using that determined SEI for a second target area of the brain, or based on a known or assumed neural characteristic of the second area, which is different from a corresponding neural characteristic of the first area, modifying the SEI for the first target area of the brain to fit the second target area of the brain.

23. The non-transitory computer readable medium of claim 12, wherein calculating the AI includes:
calculating or estimating an anisotropy of said area of the brain,
identifying a different target area of the brain,
calculating an AI for said different target area of the brain, and
using said calculated AI for said different target of the brain as the AI representative of the anisotropy of the neuronal structure within the target area.

24. The non-transitory computer readable medium of claim 12, wherein determining a base electric field amplitude and orientation for the brain includes determining a Motor Threshold (MT) for the brain.

25. A navigated Transcranial Magnetic Stimulation (nTMS) system comprising a processor configured to determine a plan for nTMS including:
determining a structural effectiveness index (SEI) for a target area of a brain which accounts for effectiveness of a Transcranial Magnetic Stimulation (TMS) pulse based on at least one neurological feature of the brain, the SEI being a function including a calculated anisotropy index (AI) representative of an anisotropy of a neuronal structure within the target area,
determining a base electric field amplitude and orientation for the brain, and
calculating an intended induced electric field for the target area of the brain based on the SEI for said target area and the base electric field amplitude and orientation.

* * * * *